United States Patent [19]

White et al.

[11] Patent Number: 4,720,454

[45] Date of Patent: Jan. 19, 1988

[54] GENETIC PROBE USED IN THE DETECTION OF ADRENAL HYPERPLASIA

[76] Inventors: Perrin C. White, 3001 Henry Hudson Pkwy., Bronx, N.Y. 10463; Bo Dupont, Braxmar Dr. S., Winfield Glen, Harrison, N.Y. 10528; Maria I. New, 435 E. 70th St., New York, N.Y. 10021

[21] Appl. No.: 601,650

[22] Filed: Apr. 18, 1984

[51] Int. Cl.$^4$ .................... C12Q 1/68; C12N 15/00
[52] U.S. Cl. .................... 435/6; 435/172.3; 536/27; 935/4; 935/9; 935/13; 935/78
[58] Field of Search .................. 435/6, 172.3; 935/13, 935/4, 9, 77, 78, 14; 536/27

[56] References Cited

U.S. PATENT DOCUMENTS 4,358,535 11/1982 Falkow et al. .................... 435/5

OTHER PUBLICATIONS

Yuan et al, PNAS, vol. 80, 1169-1173, 1983.
Marville et al, J. of Biol. Chem., vol. 258, No. 6, 3901-3906, 1983.
Fujii-Kuriyama, PNAS, vol. 79, 2793-2797, 1982.
White et al, PNAS, vol. 81, pp. 1986-1990, Apr. 1984.
White et al, PNAS, vol. 83, pp. 5111-5115, Jul. 1986.

Primary Examiner—Esther M. Kepplinger

[57] ABSTRACT

A cDNA clone is isolated encoding a bovine adrenal cytochrome P-450 specific for steroid 21-hydroxylation (P-450$_{C21}$). This plasmid pC21a contains an insert of 520 base pairs. It hybridizes with mRNA encoding P-450$_{C21}$. The peptide encoded by the insert is highly homologous to two peptides isolated from porcine P-450$_{C21}$ and shows limited homology to the P-450 induced by phenobarbital in rat liver. This probe and its human equivalents can be used to screen in utero i.e. pre-natal as well as post-natal patients for adrenal hyperplasia since it reacts well with human DNA as shown. These probes can also be useful for an industrial fermentation process to produce cortisone in quantity.

3 Claims, 9 Drawing Figures

```
                        CTG                                    TAC
BOVINE         ┌─────────┬───┬──────────────────────────────┬───┬────────┐
               │ phe ser │leu│ leu thr cys ser ile ile cys  │tyr│ leu thr│
PORCINE        │ phe ser │val│ leu thr cys ser ile ile cys  │cys│ leu thr│
               └─────────┴───┴──────────────────────────────┴───┴────────┘
                        GTG                                    TGC
                                              TTT
       ┌───────────────┬──────────────────────────────────┬───┬──────────────────┐
       │ phe gly asn   │ lys glu asp thr leu val his ala  │phe│ his asp cys val gln │
       │ phe gly ---   │ lys glu asp thr leu val his ala  │leu│ his asp cys val gln │
       └───────────────┴──────────────────────────────────┴───┴──────────────────┘
                                             TTA/G
```

GENETIC PROBE USED IN THE DETECTION OF ADRENAL HYPERPLASIA

This invention was made with government support under grants CA-22507 and CA08748 awarded by the National Cancer Institute. Therefore, the government has certain rights in this invention.

SUMMARY

This invention relates to genetic probes for adrenal hyperplasia. The publication describing some of this work is hereby incorporated by reference [White, Perrin C., et al. (1984) Proc. Nat'l. Acad. Sci. USA 81:1986.]

BACKGROUND

Deoxyribonucleic acid, DNA, consists of two paired complementary strands containing four "bases" in a particular order which specifies the amino acid sequences of various proteins and also controls when and where in the body these proteins are produced. Each human cell contains two copies of this information, each copy consisting of three billion base pairs of DNA divided between 23 chromosomes, encoding about 50,000 genes (genes on the female sex, or "X" chromosome, are present in a single copy in males). This information must be copied faithfully every time a cell divides. While the fidelity of this copying is extremely good, there are occasional errors, and DNA may also be damaged between cell divisions. If such a mutation occurs in germ cell DNA it will be inherited by that individual's offspring. If the mutation alters the function or amount of a protein, it may be evident as an inherited disease. Most often both copies of a gene must be defective (i.e., the defect must be "homozygous") to produce a detectable problem; such diseases are referred to as "autosomal recessive" disorders. When a gene is on the X chromosome, males carrying a single copy of the defective gene may be affected (a "sex-linked recessive" disorder). If "heterozygous" individuals carryiny only one defective gene are affected, the disorder is said to be "dominant".

While several thousand inherited disorders have been described, the defective protein has been identified in only a few hundred; the specific nature of the defect is known in a small fraction of these. Of clinical importance, it has often been impossible to identify heterozygous carriers of an inherited recessive disease, and after an affected child has been born in a family, it has sometimes proven impossible to prenatally diagnose future affected offspring. Cytochromes P-450 are heme-containing enzymes with molecular weights of about 50,000. They all act as terminal oxidases of NADPH-dependent electron transport pathways, but they vary as to substrate specificity and ogan distribution. Several hepatic cytochromes P-450 can be induced to high levels by xenobiotics such as phenobarbital or methylcholanthrene, and it is these enzymes that have been best characterized structurally (1) and on the molecular genetic level (2,3). A number of cytochromes P-450 in the liver, gonads, and adrenal cortex metabolize steroids. The conversion in the adrenal cortex of 17-hydroxyprogesterone to 11-deoxycortisol by 21-hydroxylation was, in fact, the first function assigned to a cytochrome P-450 (P-450) (4). Of the five steps required to synthesize cortisol from cholesterol, four require a P-450 (5): C-22,27 side chain is cleaved by a P-450 to form pregnenolone; the 3$\beta$-hydroxyl is dehydrogenated, yielding progesterone, which is successively hydroxylated by three different cytochromes P-450 at the 17$\alpha$, 21, and 11$\beta$ positions to yield cortisol. These steps occur in two subcellular locations, the side-chain cleavage and 11$\beta$-hydroxylation steps in mitochondria, and the 17$\alpha$- and 21-hydroxylations in microsomes.

In humans, genetic defects in each of the steps of cortisol biosynthesis have been described, although only in deficiency of cholesterol side-chain cleavage activity has a defective or deficient P-450 been documented (6). Of these inborn errors of metabolism, 21-hydroxylase deficiency is by far the most common, occurring in about 1/5000 individuals in most populations (7). It is inherited as a monogenic autosomal recessive trait closely linked to the HLA gene complex (8).

The HLA link is described by M. S. Pollack et al. in the Lancet May 26, 1979:

Summary

Congenital adrenal hyperplasia (C.A.H.) due to 21-hydroxylase deficiency is an HLA-linked recessive disorder. HLA-A and B antigens are expressed on amniotic cells. Prenatal diagnosis of C.A.H. by HLA typing of families and amniotic cells was attempted in two at-risk families. In one family HLA typing indicated that the fetus would have C.A.H., and this prediction was confirmed after birth. In the second family, HLA typing indicated that the fetus would be an unaffected, phenotypically normal carrier of the disease gene, and this prediction was also confirmed after birth.

Introduction

Congenital adrenal hyperplasia (C.A.H.) due to 21-hydroxylase deficiency is an autosomal recessive disease[44] in close genetic linkage with HLA. [45-51] The gene for 21-hydroxylase (21-OH) deficiency is located very close to HLA-B, and so far no genetic recombination has been demonstrated between these two loci.

Because of this close linkage with HLA, HLA typing in families with an affected member has been used to detect heterozygous carriers of the 21-OH-deficiency gene and has also resulted in the detection of previously undiagnosed homozygous 21-OH-deficiency male patients.[47,49,52] These findings indicated that HLA typing of amniotic cells could also be used to identify an affected fetus in an at-risk pregnancy. The results of HLA typing in two such pregnancies indicate that HLA typing of amniotic cells is useful for prenatal diagnosis in a pregnancy at risk for C.A.H. because of 21-OH-deficiency.

Methods

HLA typing was performed on peripheral-blood lymphocytes from the parents and all children by the standard 2-stage complement-dependent microcytotoxicity technique.

Amniotic cells taken from the mothers during the 16th week of gestation were cultured and passaged for an additional 2 weeks in Ham's nutrient mixture F-12 (containing 20% fetal calf serum, 100 units penicillin/ml, and 100 $\mu$g streptomycin/ml) to allow sufficient cell multiplication. Amniotic cells were then HLA typed by both direct and indirect (absorption/inhibition) techniques. The most suitable direct typing procedure involved plating cells for 1-2 days in the individual wells of a standard HLA typing microtitre plate. The cells were then incubated with specific antisera and complement, washed, incubated with a mixture of fluorescein diacetate and ethidium bromide, and observed with a Leitz inverted phase-contrast fluorescent microscope equipped with an I2 excitation filter for simultaneous viewing of live cells, stained green by fluorescein, and dead cells, stained red by ethidium bromide. For HLA typing of amniotic cells by absorption inhibition, specific HLA antisera were incubated with 5000 cells/µl for 1 h at room temperature, titered, and tested in parallel with unabsorbed sera for residual cytotoxic activity against a selected panel of peripheral lymphocytes positive for each serum specificity.

Amniotic-fluid concentrations of 17-hydroxyprogesterone (17-OH-P) were measured by radioimmunoassay.[53]. The parents and children of one of the two families were also tested for heterozygosity by measurement of increases in serum 17-OH-P before and 6 h after intravenous infusion of corticotropin ('Acthar', 40 units) as previously described.[52]

Case-reports

Family M.—Both parents in the family M were known heterozygous carriers of the 21-OH-deficiency gene because they had had an affected daughter. HLA typing in this family indicated that another unaffected daughter born to these parents did not carry the gene since she did not share either HLA haplotype with the affected child (FIG. 1). HLA typing of the cultured amniotic cells by both direct and indirect techniques indicated that these were HLA-identical with cells from the affected child, and it was concluded that the fetus had C.A.H. The concentration of 17-OH-P in the amniotic fluid was raised (18 ng/ml; normal 0-4 ng/ml in 43 cases) as has previously been reported in pregnancies with a fetus affected with C.A.H.[54-56] Thus, the HLA genotype of the amniotic cells and amniotic-fluid hormonal concentration suggested that the fetus was affected with C.A.H. caused by 21-OH-deficiency. The birth of an affected girl 5 months later confirmed this prediction. HLA typing of the infant's peripheral lymphocytes confirmed the predicted HLA genotype (FIG. 1).

Family L.—Both parents in family L were known to be heterozygous carriers of the 21-OH-deficiency gene since they had had an affected child, who died before being HLA typed. Two living sons were completely HLA non-identical. Their 17-OH-P responses to corticotropin stimulation were consistent with their being heterozygous carriers of the gene for 21-OH-deficiency.[52] The two possible assignments of the 21-OH-deficinecy genes to HLA haplotypes are illustrated in FIG. 2. In this family it would be possible to predict the status of the fetus based on HLA typing only if the fetus were HLA identical with one of the living unaffected children and therefore similarly unaffected. The amniotic cells were, in fact, found by both direct and indirect typing techniques to be HLA identical with cells from the second brother (FIG. 2). The amniotic fluid 17-OH-P level was normal (1-5 ng/ml; normal=0-4 ng/ml, n=43). Thus, in this family, results of HLA typing and amniotic-fluid hormone assay predicted an unaffected fetus. This prediction was also confirmed by the birth of a healthy boy whose peripheral lymphocytes expressed the predicted HLA genotype.

Discussion

The number of genetic defects which can be diagnosed prenatally by examination of either amniotic fluid or cultured amniotic cells has increased rapidly.[57] This, however, is the first report of the use of HLA typing of amniotic cells for prenatal diagnosis of any disease. HLA typing can be used for the prenatal diagnosis of C.A.H. caused by 21-OH-deficiency in a pregnancy at risk for this disorder because of the well documented close linkage of HLA with the deficiency gene and because this is a monogeneic disease in which all individuals who are homozygous for the deficiency gene are clinically affected. A few other diseases, notably C2 and C4 deficiencies,[58] have also been established as HLA-linked monogeneic conditions, but these are not always associated with clinical symptoms. HLA typing of amniotic cells for the prenatal diagnosis of other monogeneic diseases may become possible if other disease genes are found to be linked with the HLA complex.

According to Victor McKusick in *Mendelian Inheritance in Man* 4th ed., Johns Hopkins 1978 at P. 336-338:

Adrenal Hyperplasia (With Defect in Enzyme Prior to Delta 5-Pregnenolone Lipoid Hyperplasia of Adrenal Cortex with Male Pseudohermaphroditism 20, 21 Desmolase Deficiency)

The several types of adrenal hyperplasia are numbered 1 through V in order of the steps in the synthetic pathway. This form of adrenal hyperplasia is characterized in the male by various degrees of hypospadias or even almost complete failure of the external genitalia to undergo masculine development. It is believed that the genetic defect involves an enzyme necessary for the synthesis of both testicular and adrenocortical hormones. Probably the testes are unable to secrete the fetal male 'inductor' hormone which results in normal masculine genital organogenesis. The nature of the defect was stated to be unknown by Bongiovanni and Root (1963).[54] The defect is now known to concern 20, 21 desmolase, which converts cholesterol to pregnenolone. The first clue to the genetic basis of this syndrome was the observation of consanguinity in the parents of cases (Prader and Siebenmann, 1957).[62]

Adrenal Hyperplasia II (With Defect in 3-Beta-Hydroxysteroid Dehydrogenase)

Virilization is much less marked or does not occur in this type, suggesting that the gene-determined defect involves the testis as well as the adrenal. Males with the defect have hypospadias. Indeed, this form of adrenal hyperplasia can cause male pseudohermaphroditism. Salt loss is frequent cause of death. Death may occur even with adequate adrenal replacement therapy, perhaps because of the enzyme deficiency in other organs. (For another genetic disorder of the adrenal with salt loss, see ALDOSTERONE SYNTHESIS DEFECT IN.)

Adrenal Hyperplasia III (with Defect in 21-Hydroxylase)

All forms of adrenal hyperplasia show signs of excessive secretion of adrenal androgens in the form of virilization and rapid somatic advance. In some cases vomiting and dehydration resembling Addisonian crisis develop within a few weeks after birth and lead to rapid deterioration and death. Hypoglycemia sometimes occurs. Recurrent fever also may occur and may be related to etiocholanolone, although this remains to be clarified. Hypertension occurs in this form in addition to the other features. Even after being present for several years it is relieved by steroid therapy. All types of adrenal hyperplasia were reviewed exhaustively by Bongiovanni and Root (1963).[66] Prader and collegues (1962)[73] reported an enormous interlocking Swiss kindred. Two types of 21-hydroxylase defect appear to occur, one mild and one severe. In the severe form, aldosterone production is curtailed and aldosterone antagonists accumulate leading to severe salt wasting and Addisonian crisis. In females virilization is usually evident at birth. Indeed some affected females are reared as males. In the male the condition is often not recognized until late infancy or childhood. Other features of the adrenogenital syndrome are salt and water loss, hypertension, possibly fever, and Addisonian crisis. The common denominator of the several forms, in both males and females, is excessive secretion of adrenal androgens. (See PRECOCIOUS PUBERTY OF MALE in dominant catalog for simulating condition.) In the canton of Zurich, Switzerland, Prader (1958)[72] estimated the frequency to be 1 in 5041 live births, giving a frequency of carriers of 1 in 35. Childs, Grumbach and Van Wyk (1956)[67] had estimated the frequency in Maryland to be 1 in 67,000 births. A remarkable and possibly significant feature from the point of view of selection and gene frequency is the finding of Lewis et al. (1968) [70] that intelligence is increased in the adrenogenital syndrome. Merkatz et al (1969)[71] could not diagnose the disorder early in pregnancy by amniocentesis and hormone assay of the amniotic fluid. Galal et al (1969)[68] concluded that the two clinical forms of 21-hydroxylase deficiency (with and without salt-losing) correlate with the extent of the defect in the cortisol pathway. In Toronto Qazi and Thompson (1972)[74] estimated the minimum frequency of salt-losing C-21 hydroxylase deficiency as 1 per 26.292. Presumably it is a salt-losing variety of 21-hydroxylase deficiency which is present in relatively high frequency in Eskimos of Alaska (Hirschfeld and Fleshman, 1969).[69] Other recessive conditions of high frequency among the Alaskan Eskimos include Kuskokwim disease (20820), methemoglobinemia (25080), and pseudocholinesterase deficiency (27240).

Adrenal Hyperplasia IV (with Defect in 11-Beta-Hydroxylase)

When the defect involves the enzyme system concerned in hydroxylation of C11, 11-deoxycorticosterone, a potent salt-retainer, accumulates, leading to arterial hypertension. The nature of the defect was first demonstrated by Eberlein and Bongiovanni (1956)[75] on the basis of the accumulated steroids.

Therefore, methods for early detection, diagnosis and therapy are essential to minimize the spectrum of syndromes occurring with these diseases: i.e. short stature due to prematurely closed growth end plates, virilization of females, inability to produce cortisol and therefore react to stress, effects on mineral corticoid formation and therefore an increasing tendency to shock. Early detection can minimize the syndromes due to early therapy. The prevalence of the congenital defect in the population means the subject of the invention is a potential screening test for the defect.

BRIEF DESCRIPTION OF THE FIGURES

FIG. 8 shows the nucleotide sequence of pC21a and derived amino acid sequence. The positions of recognition sites of EcoRi, Pst I, and Pvu II are indicated. Also displayed are the nucleotide and derived amino acid sequences of a homologous region of pCP450-bp2 corresponding to amino acids 160–321 of P-450$_{pb}$, determined by Fugii-Kuriyama et al. (3). Asterisks indicate matching bases, and boxes, matching amino acids. Gaps have been introduced in both sequences to maximize alignment of homologous areas. The beginning and end of each homologous area are indicated by numbers below the pCP450-pb2 sequence, which refer to amino acids in P-450$_{pb}$.

FIG. 9 shows the comparison of partial amino acid sequence of porcine P-450$_{C21}$ (35) with the corresponding sequence derived from the nucleotide sequence of pC21a (in FIG. 8, this region is immediately 3' to the EcoRI site). Matching amino acids are boxed. Hypothetical nucleotide substitutions that could account for the observed differences in amino acid sequence are shown with underlines. The gap in the porcine sequence indicates an undetermined residue. The division between the two porcine peptides is indicated by the short vertical line.

DESCRIPTION

Figure 1:
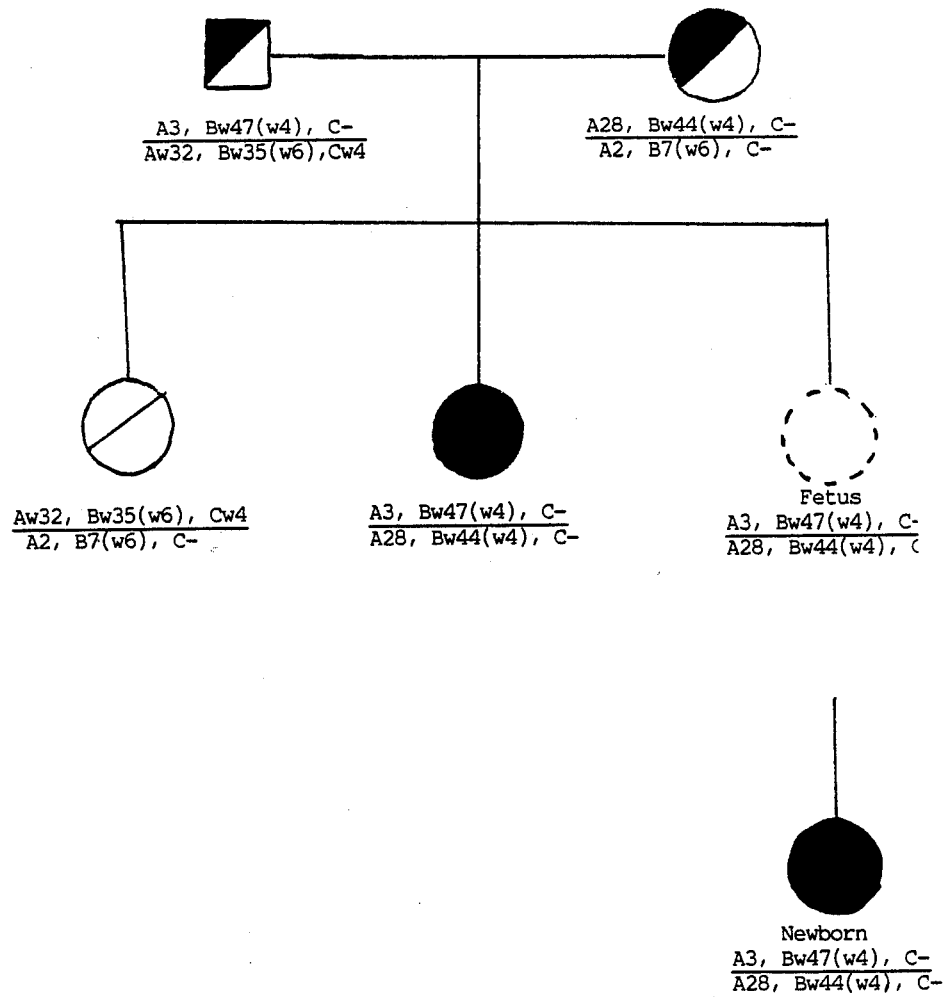
FIG. 1 shows the HLA genotypes of parents, children, and amniotic cells in family M. Shading indicates 21-OH-deficiency genes in linkage with particular parental HLA haplotypes.
Figure 2:
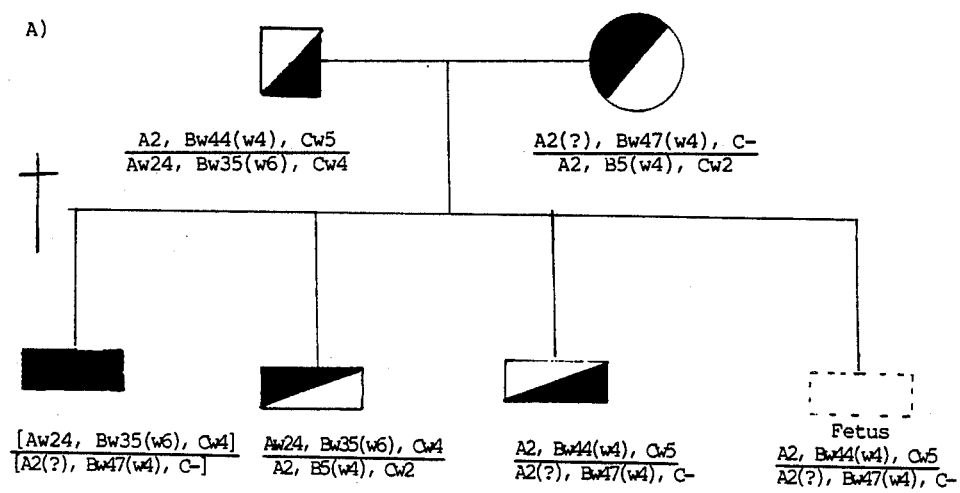
FIG. 2 shows the HLA genotypes in family L, and possible alternative HLA linkage assignments of the 21-OH-deficiency genes. Because the affected child was not HLA typed before he died, his alternative HLA antigen assignments are indicated in brackets. Assignments (FIGS. 2A and 2B) are deductions from HLA genotyping of parents.
Figure 2:
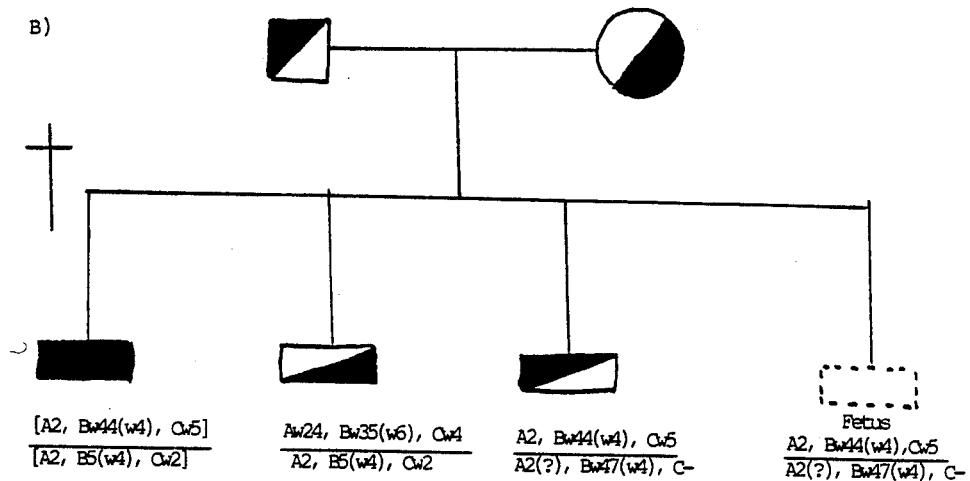

Abbreviations: P-450, cytochrome P-450; P-450$_{C21}$, cytochrome P-450 specific for steroid 21-hydroxylation; P-450$_{pb}$, cytochrome P-450 induced by phenobarbital; ds, double-stranded,; bp, base pair(s).

Because it is relatively common and has a well-defined mode of inheritance, 21-hydroxylase deficiency should be particularly amenable to study by using techniques of molecular genetics. As an initial step in such a study, we have constructed and isolated a cDNA clone corresponding to the P-450 responsible for steroid 21-hydroxylation in bovine adrenal cortex (P-450$_{C21}$). This clone encodes a polypeptide that carries antigenic determinants specific for this particular P-450.

Production of Antiserum to P-450$_{C21}$.

Bovine adrenal glands were obtained from a local slaughterhouse, frozen in liquid nitrogen, and stored at −70° C. until used. P-450$_{C21}$ was purified by the method of Kominami et al. (9). Rabbits were immunized with only four monthly injections, each containing 75 μg of purified P-450$_{C21}$ in complete (first injection) or incomplete Freund's adjuvant. The rabbits were bled 2 weeks after the last injection.

Isolation of mRNA.

Adrenal mRNA was isolated by serial ethanol precipitations from 6 M guanidine-HCl (Schwartz/Mann) (10). Poly(A)+ mRNA was isolated on oligo(dT)-cellulose (11) (Collaborative Research, Waltham, Mass.).

In vitro translations were performed with the rabbit reticulocyte lysate system (12) (Bethesda Research Laboratories) containing [$^{35}$S] methionine (New England Nuclear). Reaction products were immunoprecipitated by using anti-P-450$_{C21}$ serum and formalin-fixed *Staphylococcus aureus* (13) (Enzyme center, Boston, Mass.); the adsorbed antigen-antibody complexes were washed as described (14), eluted by boiling in sample buffer, and analyzed by NaDodSO$_4$/polyacrylamide gel electrophoresis (15) and autofluorography.

Poly(A)+ mRNA was fractionated on the basis of size by sucrose gradient sedimenation (16).

Construction of cDNA Clones.

All procedures were performed under P1, EK1 conditions of the National Institutes of Health guidelines.

Size-fractionated mRNA was reverse-transcribed into cDNA in the presence of placental ribonuclease inhibitor (17) (Boehringer Mannheim), using an oligo(dT) primer and avian myeloblastosis virus reverse transcriptase (18) (Life Sciences, St. Petersburg, Fla.). The mRNA was removed by boiling and the second strand was synthesized with DNA polymerase I (19) (New England BioLabs). Hairpin loops at the 3' ends of the first strand were removed with S1 nuclease (20) (New England Nuclear), and molecules longer than 500 base pairs (bp) were isolated by gel filtration through Sepharose 2B (Pharmacia). Terminal transferase (New England Nuclear) was used to add poly(dC) tails about 20 residues long to the recovered double-stranded cDNA (ds cDNA) (21).

Plasmid pBR322 was digested with Pst I restriction endonuclease and similarly tailed with poly(dG). Equimolar amounts of ds cDNA and linearized plasmid were annealed (22) and used to transform *E. coli* strain LE392, which had been rendered competent by a 3-hr incubation in 0.1 M CaCl$_2$ (23).

In an amount determined to yield about 500 colonies per 100-mm plate, transformed bacteria were plated onto nitrocellulose filters (HATF, Millipore) on L plates containing tetracycline at 10 μg/ml and were incubated overnight at 37° C.

Screening Transformants.

An in situ immunoassay (24,25) was used to screen for a clone expressing P-450$_{C21}$ anitgenic determinants. Anti-P-450$_{C21}$ serum was adsorbed with boiled cells of *E. coli* strain LE392 (24). Staphylococcal protein A (Pharmacia) was labeled with $^{125}$I (New England Nuclear) to a specific activity of 2×10$^7$ cpm/μg by the chloramine-T method (26). Tetracycline-resistant colonies were replicated onto additional nitrocellulose filters as described by Hanahan and Meselson (27), and the original and replica filters were incubated at 37° C. for 24 hr.

The original filters were then stored at 4° C., and the replicas were tested by a modification of the procedure of Young and David (25), similar to the method of J. Ravetch and J. Unkeless (person communication). All incubations were performed at room temperature with gentle shaking. The filters were exposed to chloroform vapor, transferred to individual Petri dishes, and treated with NaDodSO$_4$ and DNase 1 solutions as described (25). The filters were covered for 1 hr with "incubation buffer": 150 mM NaCl/50 mM tris.HCl, pH 7.8/0.5% Nonidet P-40 (Sigma)/0.5% sodium deoxycholate/0.1% NaDodSo$_4$/2% calf serum. This was removed and replaced with adsorbed antiserum, in a 1:400 dilution in incubation buffer, plus 1% of a boiled 100× concentrated stationary-phase culture of *E. coli*. After 1 hr, the filters were washed twice for 5 min per wash in incubation buffer and incubated for 1 hr with 5×10$^6$ cpm per filter of $^{125}$I-labeled protein A in incubation buffer containing 1% *E. coli* suspension. The filters were washed twice with each of the following three solutions: 0.5M NaCl/50 mM Tris.HCl, pH 7.8/0.5% Nonidet-P40, 0.15M NaCl/50 mM Tris.HCl/0.5% Nonidet-P40/0.1% NaDodSO$_4$, and 0.15M NaCl/50 mM Tris.HCl/0.5% sodium deoxycholate. The filters were dried in air and autoradiographed overnight at −70° C. by using an intensifying screen. Positive clones were selected, purified by streaking, and rescreened with the same technique.

Characterization of Plasmids.

Plasmids DNA was prepared from consistently positive clones (28). Recognition sites for restriction endonucleases (all purchased from New England BioLabs and used according to the supplier's instructions) were determined in each cDNA insert; each intact plasmid was studied with several enzymes in order to determine the orientation of the insert. Appropriate restrction fragments were subcloned in the single-stranded phage M13 mp8 or mp9 (29) and their sequences were analyzed by the Sanger-Nicklen-Coulson "dideoxy" method (30), using reagents supplied by New England BioLabs.

Purification of $P-450_{C21}$.

Figure 3:
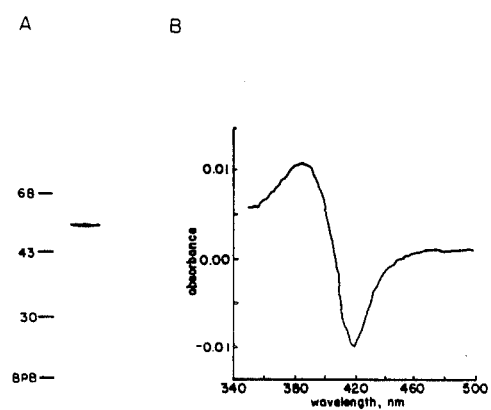
FIG. 3 shows the Purification and characterization of P-450$_{C21}$. (A) Material purified by two rounds of chromatography on 8-amino-octylagarose was subjected to electrophoresis on a NaDodSO$_4$/8.5% polyacrylamide gel. M$_r$ standards are bovine serum albumin (68,000), ovalbumin (43,000), and bovine carbonic anhydrase (30,000). The position of the bromphenol blue (BPB) dye is also indicated. (B) The spectrum of a 0.18 microM solution of P-450$_{C21}$ was determined in the presence and absence of 30 microM 17-huydroxyprogesterone and the difference is displayed.

$P-450_{C21}$ was purified to homogeneity, as judged by $NaDodSO_4$/polyacrylamide gel electrophoresis (FIG. 3A), in a yield of 1 mg from 600 g of adrenal glands. The molecular weight as determined by electrophoresis was 52,000; other investigators using the same methodology have obtained M, values of 47,000 (9) and 52,000 (31). This preparation displayed a difference spectrum characteristic of $P-450_{C21}$ (19) when the substrate 17-hydroxyprogesterone was added (FIG. 3B).

Characterization of Antiserum to $P-450_{C21}$.

Sera were obtained from a single rabbit before and after immunization with $P-450_{C21}$. These were individually mixed with a sodium cholate extract of adrenal microsomes (9) and antigen-antibody complexes were removed with formalin-fixed *S. aureus*. The supernatants were tested for in vitro 21-hydroxylase activity (32). Whereas preimmune serum had no effect, increasing amounts of immune serum removed proportionately greater amounts of 21-hydroxylase activity, with 40 μl of immune serum removing half the activity present in 1 mg of microsomal protein.

Figure 4:
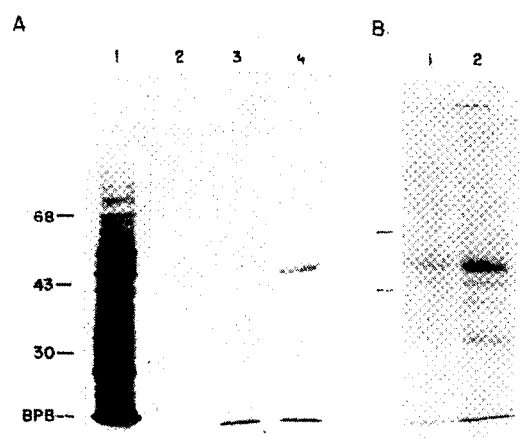
FIG. 4 shows In vitro translation of adrenal mRNA. (A) Translation of poly(A)+mRNA. Lane 1, translation products of mRNA, labeled with [$^{35}$S] methionine, separated on a NaDodSO$_4$/$_{8.5}$% polyacrylamide gel, and autofluorographed. Standards are as described for FIG. 3. Lane 2, immunoprecipitation, using immune serum, of a control reaction containing no added mRNA. Lane 3, immunoprecipitation of translation products of adrenal mRNA, using anti-P-450$_{C21}$ serum. (B) Translation of size-fractionated mRNA. Portions of two adjacent fractions from a 5-25% surcrose gradient were translated and immunoprecipitated as in A. Lane 1 represents a heavier fraction than lane 2. Lane 2 is one of two franctions at about 19S with the peak amount of P-450$_{C21}$ mRNA. Note the presence of lower molecular weight translation products in both lanes.

Immune serum specifically precipitated a single protein from the products of an in vitro translation reaction; this protein migrated with the purified $P-450_{C21}$ used for immunization (FIG. 4A).

RNA Purification.

$P-450_{C21}$-specific mRNA was detected, by in vitro translation, predominantly in 19S fractions after sucrose gadient sedimenation. Sedimentation values from 18S to 23S have been reported for other P-450 mRNAs (2, 18). While the size-fractionated mRNA was readily translatable, lower molecular weight proteins were precipitated from the in vitro translation reaction in addition to the full-length translation product (FIG. 4B). These low molecular weight bands were assumed to represent termination of translation at defined points. They were not seen when translating unfractionated mRNA and so were unlikely to be proteolytic degradation products. If mRNA were being degraded during fractionation, there should have been an increased proportion of the low molecular weight bands in translations of slower-sedimenting (smaller) mRNA; instead, in translations of different size fractions, the lower molecular weight bands varied in intensity in proportion to the amount of the full-length translation product. This phenomenon has been ascribed to aggregation of a particular mRNA with itself or with other mRNAs or to unknown contaminants that inhibit translation (33).

cDNA Cloning.

One microgram of size-fractionated mRNA was reverse transcribed into approximately 100 ng of ds cDNA. Molecules longer than about 500 bp made up 20 ng. After oligo(dC) tailing and annealing with 100 ng of linearized vector, this preparation transformed LE392 cells at an efficiency of approximately 1000 transformers per ng of ds cDNA.

Figure 5:
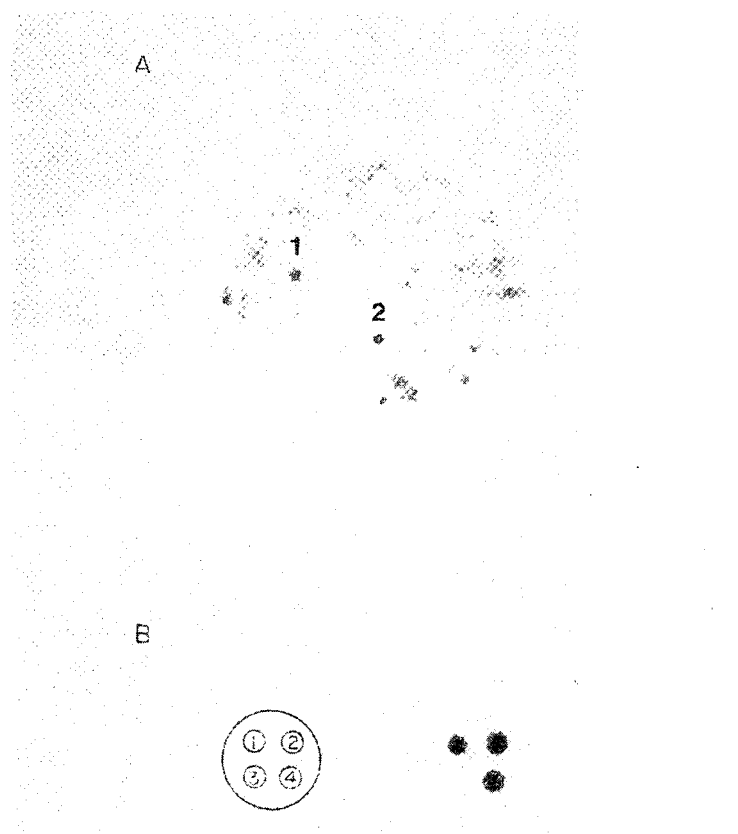
FIG. 5 shows In situ immunologic screening of bacterial colonies. (A) First round of screening. Autoradiogram of a replica of 1 of 16 filters after lysis with chloroform and incubation with immune serum and $^{125}$I-labeled protein A. Numbers indicate positions of two colonies on this plate selected for further testing. (B) Testing of same two clones after purification. Positions 1 and 2 are the clones of A; position 3 is a clone carrying a different, uncharacterized, plasmid. These colonies were 3 mm in diameter. Position 4, 10 pg of purified P-450$_{C21}$ spotted onto filter prior to chloroform treatment.

Approximately 8000 colonies were screened with the in situ immunoassay. Two colonies from a single plate consistently bound antiserum and $^{125}I$-labeled protein A as detected by autoradiography (FIG. 5A). The amount of protein A bound by each colony was equivalent to that bound by less than 10 pg of purified $P-450_{C21}$ (FIG. 5B).

These two colonies carried plasmids with inserts of identical size and pattern of recognition sites for several restriction enzymes (FIG. 6) and thus are presumably descendents of the same transformant. One clone, designated pC21a, was compared with pBR322 by hybrid-selected translation (34). RNA hybridizing to pC21a encoded a protein, precipitated by anti-$P-450_{C21}$ serum, of identical size to purified $P-450_{C21}$ (FIG. 7). In addition to the full-length translation product, lower molecular weight bands were noted in a pattern very similar to the pattern seen on translating size-fractionated adrenal mRNA (i.e., premature termination of translation; compare with FIG. 4B).

DNA Sequence Analysis.

Figure 6:
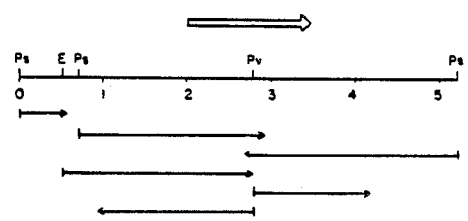
FIG. 6 shows a map of pC21a. Large arrow indicates direction of transcription in the beta-lactamase gene of pBR322. Numbers indicate length in hundred of bp. Recognition sites for restriction enzymes are indicated: Ps, Pst I; E, EcoRI; Pv, Pvu II. Fragments subcloned in M13 mp8 and mp9 are diagrammed below. Arrows indicate direction of transcription during sequencing reactions.
Figure 7:
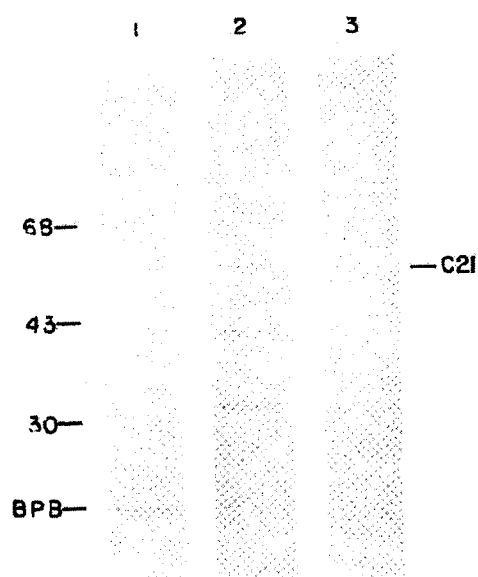
FIG. 7 shows a hybrid-selected translation by pC21a: immunoprecipitations of products of in vitro translations, as in FIG. 4. The position of P-450$_{C21}$ is indicated. Lane 1, translation of adrenal mRNA. Lane 2, translation of mRNA selected by hybridization to pC21a (compare pattern to FIG. 4B). Lane 3, translation of mRNA selected by hybridization of pBR322.

The sequences of restriction fragments of pC21a subcloned in M13 mp8 and mp9 were determined as diagrammed in FIG. 6. The sequence from the EcoRI site to the 5′ end of the insert was also determined by the Maxam-Gilbert method (35).

Figure 8:
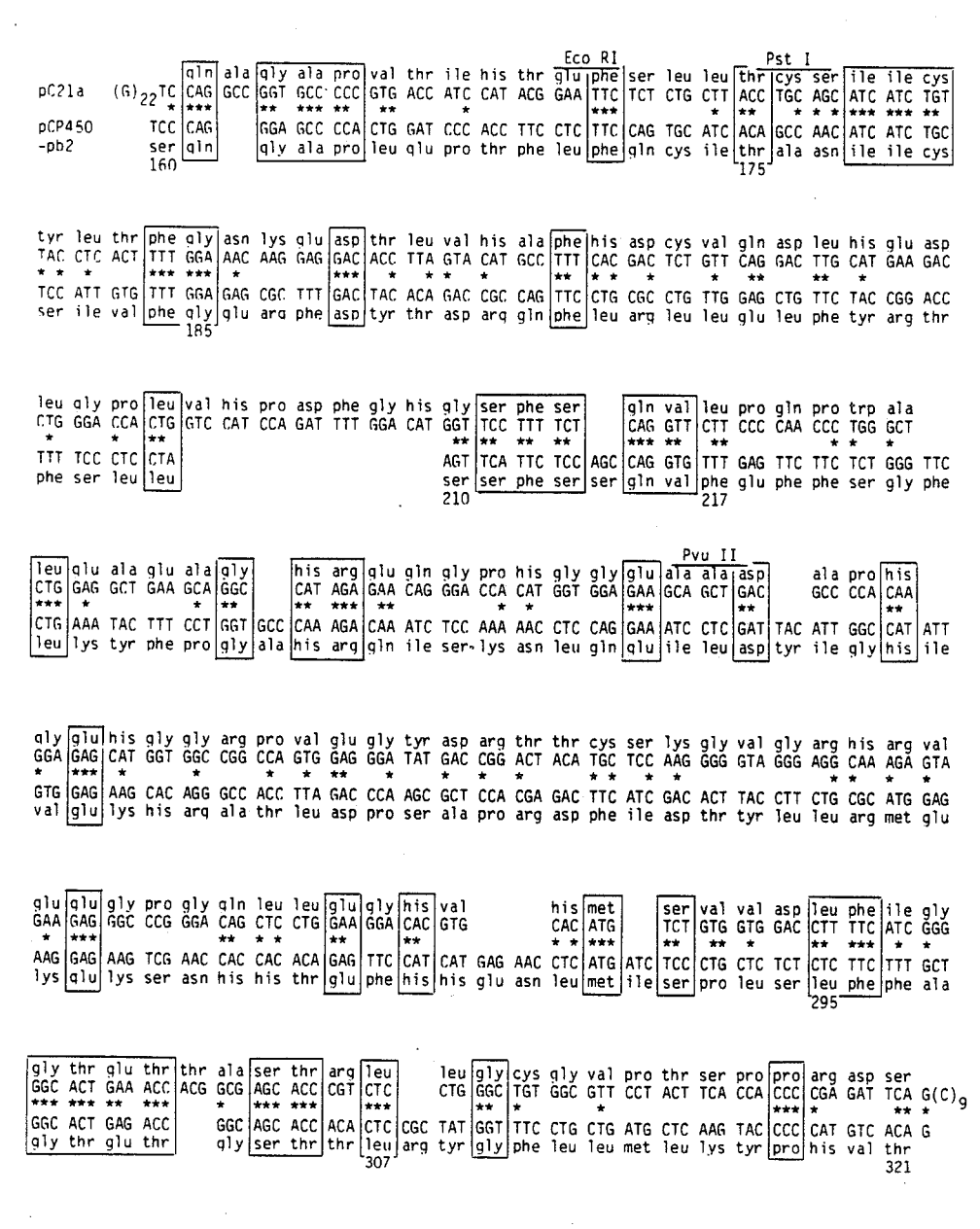

The nucleotide sequence of pC21a is displayed in FIG. 8. The cDNA insert of pC21a contains 520 bp, including homopolymer tails of 22 and 9 bp. There is a single open reading frame spanning the entire insert, which is in the same orientaton and frame as the β-lactamase gene (22) into which the cDNA has been inserted.

There are no amino acid sequence data for bovine $P-450_{C21}$ available to compare with the amino acid sequence derived from the DNA sequence of pC21a. However, the sequences of the cysteine-containing peptides of the porcine enzyme have recently been determined (36), and in FIG. 9 the sequences of two peptides are compared with the corresponding derived amino acid sequence from pC21a. These two peptides show 90% homology to a single continous sequence in the bovine enzyme consisting of 30 amino acids; each of the three differences between the bovine and porcine sequences can be accounted for by a single nucleotide substitution. The remaining five cysteine-containing peptides from porcine $P-450_{C21}$ exhibit no homology to the derived amino acid sequence of pC21a and may represent portions of the protein not encoded by pC21a.

Because the amino acid sequence data for porcine $P-450_{C21}$ are limited, we have also compared (FIG. 8) the nucleotide and derived amino acid sequences of pC21a and a cDNA clone, pCP450-pb2 (3), encoding the P-450 induced by phenobarbital in rat liver [referred to here as $P-450_{pb}$, although there are in fact two closely related isozymes (1,3)]. Significant homology is found between pC21a and the region of pCP450-pb2 encoding amino acids 160–321 of P-450$_{pb}$, which is approximately the middle third of the protein. This homology is concentrated in three limited areas, corresponding to amino acids 175–185, 210–217, and 295–307 in P-450$_{pb}$.

There is approximately 65% nucleotide homology between pC21a and pCP450-pb2 within these areas. Overall, there is 35% nucleotide sequence homology, and 25% of the amino acids encoded by pC21a match those of pCP450-pb2.

We have isolated a cDNA clone, pC21a, that causes *E. coli* to express P-450$_{C21}$ antigenic determinants, presumably on a fusion protein encoded by a pBR322 β-lactamase gene containing a 500-bp cDNA insert. The insert in pC21a has been identified as a part of the P-450$_{C21}$ structural sequence because it hybridizes mRNA encoding a protein of the same size as P-450$_{C21}$ that is precipitated by anti-P-450$_{C21}$ serum. The DNA sequence of pC21a confirms this identification, because the derived amino acid sequence shows high homology to the sequences of two peptides isolated from porcine P-450$_{C21}$.

In principle, another adrenal P-450 might be sufficiently similar to P-450$_{C21}$ to crossreact antigenically and/or confuse the results of the hybrid-selected translation experiment and the sequence comparisons. Of the other known adrenal cytochromes P-450, P-450$_{vcc}$, and P-450$_{11\beta}$ are mitochondrial in origin, do not crossreact antigenically with P-450$_{C21}$ (9), and are unlikely to be contaminating the purified microsomal protein preparation used for immunizations. P-450$_{17a}$, a microsomal protein, is reported to be about 2000 daltons lighter than P-450$_{C21}$ and has a quite different amino acid composition (31). Finally, pC21a appears to hybridize under conditions of moderate stringency (65° C., 0.15M NaCl) to a single fragment of about 20 kilobase pairs in a HindIII digest of bovine genomic DNA (unpublished observations). Thus, there does not seem to be any P-450 in the bovine adrenal that could be confused with P-450$_{C21}$.

The nucleotide and amino acid sequence homologies between pC21a and pCP450-pb2, 35% and 25%, respectively, while significant, are limited; they are similar to the homologies between rat growth hormone and prolactin (39% and 24%) (37). Several regions of P-450 are in general more highly conserved, including, in rat P-450$_{pb}$, amino acids 145–158 (38), 346–358 (39), and 435–445 (36). None of these are within the area homologous to pC21a. Outside such regions, the homologies between different cytochromes P-450 seem to vary considerably. For example, cDNA clones encoding the two closely related forms of rat P-450$_{pb}$ (1) differ in less than 3% of their sequence (3). A similar clone showed no hybridization to mRNA encoding two cytochromes P-450 induced, respectively, by methycholanthrene and isoafrole, which, however, were immunochemically related to each other (40). This clone ("R17," kindly provided by Milton Adesnik, New York University Medical School) also fails to hybridize in "northern" blots (41) to bovine adrenal mRNA, even under low-stringency conditions (50° C., 0.5 M NaCl) (unpublished observations). This is consistent with the 35% nucleotide homology noted between pC21a and pCP450-pb2. Nucleic acid sequence data are clearly indispensable in the study of relationships between cytochromes P-450, and they show in this case that although P-450$_{C21}$ and P-450$_{pb}$ are not part of a single "family" of genes, they are members of the same "superfamily" (42).

In contrast to the often limited homology between different cytochromes P-450, the structure of a P-450 with a particular substrate specificity does appear to be highly conserved in different species. Cloned cDNA for mouse methylcholanthrene-induced P-450 hybridizes to human genomic DNA and has been used to isolate genomic clones containing two separate genes (43). Limited comparison of bovine and porcine P-450$_{C21}$ reveals 90% homology of amino acid sequences. Because the bovine (31) and porcine (36) enzymes also have very similar amino acid compositions, the complete sequences will probably show a similar high level of homology. It seems likely that pC21a will hybridize to the homologous genes in other species, including man; it should therefore be a useful reagent in studying the molecular basis of 21-hydroxylase deficiency.

In addition, we describe work in human patients.

Congenital adrenal hyperplasia due to 21-hydroxylase (21-OH) deficiency is a common inherited disorder of steroidogenesis that is HLA-linked. The biochemical defect has never been directly determined. In vitro 21-OH activity can be produced with two microsomal proteins from the adrenal cortex, an NADPH-dependent cytochrome reductase and a cytochrome P-450. As only the P-450 is substate-specific, we hypothesized that the HLA-linked defect involved a structural gene for this protein.

After reverse-transcribing mRNA from bovine adrenal glands, we isolated a plasmid with a 520 bp cDNA insert encoding the middle third of the P-450 peptide [White et al. PNAS April 1984]. We used this plasmid to search for restriction fragment polymorphisms is patients with 21-OH deficiency. The haplotype HLA-(A3); Bw47; DR7 is strongly associated with 21-OH deficiency and always carries a null allele at the complement C4A (Rodgers) locus. It seems likely that this haplotype carried a deletion encompassing both the C4A and 21-OH loci. When human DNA was digested with Taq I restriction endonuclease and hybridized under moderately stringent conditions with the cDNA probe, DNA from 13 unrelated normal individuals yielded two hybridizing bands of equal intensity at 3.7 and 3.2 kb. The upper band was not present in DNA from a patient homozygous for Bw47. DNA from six unrelated patients heterozygous for Bw47 yielded, in five, diminished relative intensity of the upper band consistent with a heterozygous deletion, and complete disappearance of the upper band in one ($X^2 = 15.9$, $p = 0.0001$). Linkage of this polymorphism to HLA was examined in the families of several of these patients; the lod score thus far exceeds 2.0 at a recombinant fraction of 0.0. Thus a structural gene for 21-hydroxylase (a cytochrome P-450) is mapped to the HLA complex; 21-OH deficiency sometimes results from the deletion of this gene and sometimes, presumably, from smaller mutations. This gene is probably located very near the C4A gene encoding the fourth component of complement.

Furthermore, this invention includes all equivalent nucleic acid probes. The examples and results shown are illustrative of the invention and are not meant to limit it. It will be obvious to those skilled in the art that equivalent probes whether of RNA or DNA can be produced following the teaching of the Invention.

With new technology, it is now possible to identify defective genes; often the actual mutation, even if it involves a single base, may be detected. It may be instructive to describe the process for a specific example.

We have recently determined the molecular basis of congenital adrenal hyperplasia due to steroid 21-hydroxylase deficiency. This is a relatively common autosomal recessive disorder, occurring in 1/5000 persons in this country; it is about three times as common as phenylketonuria (PKU) for which screening is mandated by law on all births in this state. Individuals with 2-hydroxylase deficiency have a defect in one of the enzymes which synthesize cortisol from cholesterol; in attempting to compensate for the defect, the adrenal glands synthesize excessive androgens, which may cause girls to be born with external genitalia resembling males and may cause growth disturbances in either sex. There is often defective salt metabolism, which if untreated may result in shock or death.

When we began this study, we didn't know which protein was defective in 21-hydroxylase deficiency. We did know that the defective gene was located very near (i.e., "linked" to) the genes encoding the "HLA" transplantation antigens, because if two children in the same family both had the disease, they had identical HLA antigens on their white blood cells. This also made it very easy, by HLA typing, to detect heterozygous carriers in any given family once the HLA type of the patient was known.

It was also known that the 21-hydroxylase enzyme activity could be reproduced in the test tube with two proteins purified from animal adrenal glands. One of these proteins was involved in many different hydroxylation reactions, whereas the other, a type of enzyme termed a cytochrome P-450, was specific for hydroxylation of several steroids at the "21" position. We hypothesized that this second protein was defective in 21-hydroxylase deficiency, and set about "cloning" part of the gene encoding this enzyme. As a first step, we purified the cytochrome P-450 from cow adrenal glands and injected the protein into rabbits to produce an antiserum which specifically bound the enzyme.

To understand the cloning procedure, it should be remembered that the DNA in each cell contains the instructions to synthesize all proteins made anywere in the body, but that these instructions (or "coding regions") are not read directly off the DNA molecule. Instead, a single-stranded intermediate copy, termed "messenger ribonucleic acid", or "mRNA", is made from the appropriate portion of one strand of the DNA molecule. This copy is then processed to remove intervening sequences that are found within the coding regions, and transported out of the nucleus to the ribosomal protein synthesizing apparatus of the cell. Because only a small fraction of the body's proteins are synthesized in any given cell, a correspondingly small fraction of the cell's DNA is copied into mRNA.

Certain cancer viruses contain an enzyme which allows mRNA molecules to be copied, or "reverse-transcribed", back into DNA. This synthetic DNA is complementary to the mRNA sequence, and is termed "complementary" DNA, or "cDNA". It differs from the genes as found on the chromosomes in that it lacks the intervening and flanking sequences which have been processed out of the mRNA molecules. This means that cDNA, unlike mammalian chromosonal DNA, can be transcribed by bacteria.

We extracted the mRNA from cow adrenal glands, and synthesized cDNA from the mRNA mixture using "reverse-transcriptase" and other enzymes. This was inserted into molecules of a "plasmid". Plasmids are small (a few thousand base pairs) circular DNA molecules which can replicate autonomously in bacteria, and which carry genes for resistance to anitbiotics. Bacteria carrying the plasmids could thus be selected by means of antibiotic resistance. The cDNA molecules were inserted into the middle of a gene carried on the plasmid which encoded an enzyme which destroys penicillin. Under these circumstances, inserted DNA might result in synthesis of a hybrid protein containing part of the protein encoded by the cDNA insert and part of the penicillinase enzyme.

At this point, cDNA copies of all the adrenal mRNA molecules were present as a mixture. This mixture of plasmid-cDNA "recombinants" was inserted into E. coli bacteria under conditions where each bacterial cell would receive at most one plasmid molecule. When atibiotic-resistant cells were grown on petri dishes, all the cells in each bacterial colony were descended from a single cell, and thus carried the same plasmid. By growing cells from a colony in a larger culture, any amount of any individual plasmid could be obtained.

We examined several thousand colonies to see if any bound the specific antiserum to the cytochrome P450, and found one. This colony, or "clone", thus consisted of bacterial cells carrying a plasmid which contained a cDNA insert which was a copy of the mRNA encoding the cytochrome P-450 (!); these cells made a hybrid protein which bound the antiserum to the cytochrome P-450 protein.

We have recently used this plasmid clone to study the DNA of patients with 21-hydroxylase deficiency and their families. We have concentrated on patients carrying the HLA-Bw47 antigen, which is strikingly increased in frequency among patients with 21-hydroxylase deficiency and which invariably is also associated with a partial deficiency of a serum protein, the fourth component of complement. Because the same chromosome carries two different deficient genes, it seemed likely that there was a significant deletion or rearrangement of DNA, rather than a point mutation that might be more difficult to detect.

We extracted DNA from human white blood cells and digested it with one of several bacterial enzymes, termed "restriction endonucleases", which cut DNA at specific sequences. These "recognition sites" are four or six bases long and occur once every few thousand bases; they have no functional significance as such in human DNA. The resulting fragments were fractionated on the basis of size by electrophoresis in an agarose gel; DNA, being negatively charged, moved toward the positive pole in an electric field, and smaller molecules moved more quickly through the agarose. The fragments were denatured by exposure to alkali (i.e., changed from the noraml double-stranded configuration to a single stranded form) and blotted onto a sheet of nitrocellulose. Plasmid DNA was radioactively labelled, then also denatured, and incubated with the nitrocellulose sheet under conditions where double-stranded DNA could re-form. Where there was sufficient similarity between the radioactive "probe" DNA and the human DNA fragments bound to the nitrocellulose, the probe formed a "hybrid" with the bound DNA. This could be detected by autoradiography. We assumed that the human and cow genes were similar enough that the probe derived from cow adrenal mRNA would bind human DNA.

When this procedure was performed using DNA from normal individuals, two bands (presumably two genes) were seen on the X-ray film after digestion with an appropriate restriction enzyme and hybridization with the plasmid. In an individual homozygous for HLA-Bw47, one band disappeared completely. In individuals heterozygous for this antigen, that band was reduced in intensity consistent with a heterozygous deletion; one patient who was Bw47 heterozygous nevertheless carried a homozygous deletion of this gene.

Thus 21-hydroxylase deficiency indeed appears to be associated with a defect in a structrual gene for the specific cytochrome P-450; sometimes this defect is a deletion of the gene, and sometimes the defect is more subtle, possibly a point mutation. This is not surprising, considering that the disease varies considerably in severity, and that more or less severe forms are associated with different HLA antigens. If we use different restriction enzymes, we expect to find instances where a recognition site is formed or deleted by a mutation, which will result in change of size of a hybridizing band. This phenomenon is referred to as a "restriction fragment length polymorphism", and can allow for detection of many single base mutations.

Enough material can be harmlessly obtained from a growing fetus by amniocentesis or chorionic villus biopsy to perform DNA studies, which can allow for prenatal diagnosis once a DNA polymorphism has been identified in a particular family, and heterozygous carriers can also be identified. These techniques have been applied to several other inherited diseases including defects in hemoglobin synthesis (sickle cell anemia and the thalassemias), phenylketonuria, and Huntington's Disease.

For diagnostic purposes, it may sometimes be unnecessary to identify the actual defective gene. Just as HLA typing can be used to study families with 21-hydroxylase deficiency, DNA polymorphisms that are linked to a defective gene may be useful as long as they are sufficiently near (within several million base pairs of) the gene in question. Such linked polymorphisms, of course, merely determine location of a defective gene and indicate nothing about the nature of the defect.

A human-human probe using a human clone containing the 17-OH gene is also made using the above methods and a cosmid library which plasmid is preferentially expressed in eucaryotic cells.

Plasmid pC21a and the human probe(s) pC21a are maintained on deposit at Sloan-Kettering Institute for Cancer Research, 1275 York Avenue, New York, N.Y.

Plasmid pC21a has been deposited on Apr. 18, 1984 with the American Type Culture Collection (ATCC), 12301 Parklawn Drive, Rockville, Md. 20852 under ATCC designation 39663.

REFERENCES

1. Yuan, P. M., Ryan, D. E., Levin, W. & Shively, J. E. (1983) Proc. Natl. Acad. Sci. USA 80, 1169-1173.
2. Negishi, M., Swan, D. C., Enquist, L. W. & Nebert, D. W. (1981) Proc. Natl. Acad. Sci. USA 78, 800-804.
3. Fujii-Kuriyama, Y., Mizukami, Y., Kawajiri, K., Sogawa, K., & Muramatsu, M. (1982) Proc. Natl. Acad. Sci. USA 79, 2793-2797
4. Estabrook, R. W., Cooper, D. Y. & Rosenthal, O. (1963) Biochem Z. 338, 741-755.
5. Finkelstein, M. & Shaefer, J. M. (1979) Physiol. Rev. 59, 353-406.
6. Koizumi, S., Kyoka, S., Miyawaki, T., Kidani, H., Funabashi, T., Nakashima, H., Nakanuma, Y., Ohta. G., Itagaki., C. & Katagiri, M. (1977) Clin. Chim. Acta 77, 301-306.
7. New, M. I., Dupont, B., Grumbach, K. & Levine, L. S. (1982) in The Metabolic Basis of Inherited Disease, eds. Stanbury, J. B., Wyngaarden, J. B., Fredrickson, D. S., Goldstein, J. L. & Brown, M.S. (McGraw-Hill, New York), pp. 973-1000.
8. Dupont, B., Oberfield, S. E., Smithwick, E. M., Lee, T. D. & Levine, L. S. (1977) Lancet ii, 1309-1311.
9. Kominami, S., Ochi, H., Kobayashi, Y. & Takemori, S. (1980) J. Biol. Chem. 255, 3386-3394
10. Strohman, R. C., Moss. P. S., Micou-Eastwood, J., Spector, D., Przybyla, A. & Paterson, B. (1977) Cell 10, 256-273.
11. Efstratiadis, A. & Kafatos, F. (1976) in Methods in Molecular Biology, ed, Last, J.A. (Dekker, New York), pp. 1-124.
12. Pelham, H. R. & Jackson, R. J. (1976) Eur. J. Biochem. 67,247-256.
13. Kessler, S. W. (1975) J. Immunol. 115, 1617-1624.
14. Schneider, C., Newman, R. A., Asser, U., Sutherland, D. R. & Greaves, M. F. (1982) J. Biol. Chem. 257, 10766-10769.
15. Laemmli, U. K. (1970) Nature (London) 227, 680-685.
16. Fujii-Kuriyama, Y., Taniguchi, T., Mizukami, Y., Sakai, M., Tashiro, Y. & Muramatsu, M. (1981) J. Biochem. (Tokyo) 89, 1869-1879.
17. deMartynoff, G., Pays, E. & Vassart, G. (1980) Biochem. Biophys. Res. Commun. 93, 645-653.
18. Buell, G. N., Wickens, M. P., Payvar, F. & Schimke, R. T. (1978) J. Biol. Chem. 253, 2471-2482.
19. Wickens, M. P., Buell, G. N. & Schimke, R. J. (1978) J. Biol. Chem. 253, 2483-2495.
20. Goodman, H. M. & MacDonald, R. J. (1979) Methods Enzymol. 68, 75-90.
21. Deng, G. & Wu, R. (1981) Nucleic Acids Res. 9, 4173-4188.
22. Villa-Komaroff, L. Efstratiadis, A., Broome, S., Lomedico, P., Tizard, R., Naber, S. P., Chick, W. L. & Gilbert, W. (1978) Proc. Natl. Acad. Sci. USA 75, 3727-3731.
23. Dagert, M. & Ehrilich, S. D. (1979) Gene 6, 23-28.
24. Helfman, D. M., Feramisco, J. R., Fiddes, J. C., Thomas, G. P. & Hughes, S. H. (1983) Proc. Natl. Acad. Sci. USA 80, 31-35.
25. Young, R. A. & Davis, R. W. (1983) Proc. Natl. Acad. Sci. USA 80, 1194-1198.
26. McConahey, P. J. & Dixon, F. J. (1966) Int. Arch. Allergy Appl. Invest. 29, 185.
27. Hanahan, D. & Meselson, M. (1980) Gene 10, 63-67.
28. Herschfield, V., Boyer, H. W., Yanofsky, C., Lovett, M. A. & Helinski, D. R. (1974) Proc. Natl. Acad. Sci. USA 71, 3455-3460.
29. Messing, J. (1981) in Recombinant DNA: Proceedings of the Third Cleveland Symposium on Macromolecules, ed. Walton, A. G. (Elsevier/North-Holland, Amsterdam), pp. 143-153.
30. Sanger, F., Nicklen, S. & Coulson, A. R. (1977) Proc. Natl. Acad. Sci. USA 74, 5463-5467.
31. Bumpus, J. A. & Dus, K. M. (1982) J. Biol. Chem. 257, 12696-12704.
32. Chasalow, F. I. & Lieberman, S. (1979) J. Biol. Chem. 254, 3777-3781.
33. Payvar, F. & Schimke, R. T. (1979) J. Biol. Chem. 214, 7636-7642.

34. Parnes, J. R., Velan, B., Felsenfeld, A., Ramanathan, L., Ferrini, V., Appelu, E. & Seidman, J. G. (1981) Proc. Natl. Acad. Sci. USA 78,2253-2259.
35. Maxam, A. M. & Gilbert, W. (1980) Methods Enzymol. 65, 499-559.
36. Yuan, P. M., Nakajin, S., Haniu, M., Shinoda, M., Hall, P. F. & Shively, J. E. (1983) Biochemistry 22, 143-149.
37. Cooke, N. E., Coit, D., Weiner, R. J., Baxter, J. D. & Martial, J. A. (1980) J. Biol. Chem. 255, 6502-6510.
38. Black, S. D., Tarr, G. E. & Coon, M. J. (1982) J. Biol. Chem. 257, 14616-14621.
39. Ozols, J., Heineman, F. S. & Johnson, E. F. (1981) J. Biol. Chem. 256, 11405-11408.
40. Morville, A. L., Thomas, P., Levin, W., Reik, L., Ryan, D. E., Raphael, C. & Adesnik, M. (1983) J. Biol. Chem. 258, 3901-3906.
41. Maniatis, T., Fritsch, E. F. & Sambrook, J. (1982) Molecular Cloning: A Laboratory Manual (Cold Spring Harbor Laboratory, Cold Spring Harbor, NY) pp. 202-203.
42. Dayhoff, M. O., Barker, W. C., Hunt, L. T. & Schwartz, R. M. (1978) in Atlas of Protein Sequence and Structure, ed. Dayhoff, M.O. (Natl. Biomed. Res. Found., Washington, DC), Vol. 5 Suppl. 3, pp. 9-10.
43. Chen, Y. T., Tukey, R. H., Swan, D. C., Negishi, M. & Nebert, D. W. (1983) Pediatr. Res. 17, 208A (abstr.). 44. McKusick, V.A., Mendelian Inheritance in Man. p. 403, Baltimore, 1978.
45. Dupont, B., Oberfield, S. E., Smithwick, E. M., Lee, T. D., & Levine, L. S., Lancet, 1977 ii, 1309.
46. Levine, L. S., Zachmann, M. & New, M. I., et al. New Engl. J. Med. 1978, 299, 911.
47. Price, D. A., Klouda, P. T. & Harris, R., Lancet, 1978, i, 930.
48. Weitkamp, L. R., Bryson, M. & Bacon, G. E., Lancet, 1978, i, 930.
49. Zappacosta, S., DeFelice, M., Minozzi, M., Lombardi, G., Valentino, R. & Vanacore, G., Lancet, 1978, ii, 524.
50. Murtaza, L. M., Hughes, I. A., Sibert, J. R. & Balfour, I. C., Lancet, 1978, ii, 524.
51. Pucholt, V., Fitzsimmons, J. S., Gelsthorpe, K., Pratt, R. F. & Doughty, R. W., Lancet, 1978, ii, 1046.
52. Lorenzen, F., Pang, S., New, M. I., Dupont, B., Chow, D. & Levine, L. S., Pediot. Res. (in press).
53. Pang, S., Hutchkiss, J., Drash, A. L., Levine, L. S & New, M. I. J., Clin. Endocr. Metab. 1979, 45, 1003.
54. Frasier, S. D., Thorneycroft, I. H., Weiss, B. A. & Horton, R. J., Pediat, 1975, 86, 310.
55. Milunsky, A. & Tulchinsky, D., Pediatrics, 1977, 59, 768.
56. Nagamani, M., McDonough, P. G., Ellegood, J. O. & Mahesh, V. B., Am. J. Obster. Gynec. 1978, 130, 791.
57. Omenn, G. S., Science, 1978, 200, 952.
58. Dupont, B., O'Niell, G. J., Yang, S. Y., Pollack, M. S. & Levine, L. S., In Genetic Control of Autoimmune Disease (edited by N. R. Rose, P. E. Bigazzi, and N. L. Warner); p. 15, Amsterdam. 1978.
59. Bongiovanni, A. M. & Root, A. W., New Eng. J. Med. 268: 1283-1289, 1351, and 1391-1399, 1963.
60. Camacho, A. M., Kowarski, A., Migeon, C. J. & Brough, A. J., & J. Clin. Endocr. 28: 153-161, 1968.
61. Prader, A. & Anders, G. J. P. A., Helv. Paediat. Acta. 17: 285-289, 1962.
62. Prader, A. & Siebenmann, R. E., Helv. Paediat. Acta 12: 569-595, 1957.
63. Bongiovanni, A. M., J. Clin. Invest. 41: 2086-2092, 1962.
64. Hamilton, W. & Brush, M. G., Arch. Dis. Child. 39: 66-72, 1964.
65. Bongiovanni, A. M.: Disorders of Adrenocortical Steroid Biogenesis. In, Stanbury, J. B., Wyngaarden, J. B. and Fredrickson, D. S. (eds.): The Metabolic Basis of Inherited Disease. New York: McGraw-Hill, 1972 (3rd Ed.) pp. 857-885.
66. Bongiovonni, A. M. & Root, A. W., New Eng. J. Med. 268: 1283-1289, 1342-1351, And 1391-1399, 1963.
67. Childs, B., Grumbach, M. M. & Van Wyk, J. J., J. Clin. Invest. 35: 213-222, 1956.
68. Galal, O. M., Rudd, B. T. & Drayer, N. M., Arch. Dis. Child. 43: 410-414, 1969.
69. Hirschfeld, A. J. & Fleshman, J. K., J. Pediat. 75: 492-494, 1969.
70. Lewis, V. G., Money, J. & Epstein, R., Johns Hopkins Med. J. 122: 192-195, 1968.
71. Merkatz, I. R., New, M. I., Peterson, R. E. & Seaman, M. P., J. Pediat. 75: 977-982, 1969.
72. Prader, A., Helv. Paediat. Acta 13: 426-431, 1958.
73. Prader, A. & Anders, G. J. P. A. Habich, H., Helv. Paediat. Acta. 17: 271-284, 1962.
74. Qazi, Q. H. & Thompson, M. W., Arch. Dis. Child. 47: 302-303, 1972.
75. Eberlein, W. R. & Bongiovanni, A. M., J. Biol. Chem. 223: 85-94, 1956.
76. Visser, H. K. A. Inherited Variation in the Biosynthesis of Adrenal Corticosteroids in Man. In, Endocrine Genetics. Spickett, S.G. (ed.): Mem. Soc. Endrocrinology, 1967, pp. 145-178.

What is claimed:

1. cDNA probe pC21a (ATCC 39663) capable of binding to genomic human DNA diagnostic for congenital C21 hydroxylase deficiency adrenal hyperplasia in humans.

2. cDNA probe of claim 1 wherein the cDNA is produced using reverse transcriptase from bovine mRNA specific for cytochrome C-21 hydroxylase P-450.

3. Method for detection of congenital adrenal hyperplasia C-21 hydroxylation defect in humans which comprises:
contacting samples of human genomic DNA with a labelled pC21a cDNA probe (ATCC 39663) specific for genomic DNA coding for cytochrome P-450 steroid 21 hydroxylase for a time and under conditions sufficient to effect hybridization and observing the presence or absence of labelled probe binding to the genomic DNA, the absence of binding indicating a congenital adrenal hyperplasia C-21 hydroxylation defect.

* * * * *

UNITED STATES PATENT AND TRADEMARK OFFICE
CERTIFICATE OF CORRECTION

PATENT NO. : 4,720,454

DATED : January 19, 1988

INVENTOR(S) : Perrin C. White, et al.

It is certified that error appears in the above-identified patent and that said Letters Patent is hereby corrected as shown below:

On the cover page, after [75] Inventors section insert:

--[73]  Assignee:  Sloan-Kettering Institute for Cancer Research, New York, N.Y.; and Cornell Research Foundation, Inc., Ithaca, New York--

Signed and Sealed this

Eighth Day of November, 1988

*Attest:*

DONALD J. QUIGG

*Attesting Officer*  *Commissioner of Patents and Trademarks*